United States Patent
Buchecker et al.

(10) Patent No.: US 6,277,502 B1
(45) Date of Patent: Aug. 21, 2001

(54) PHOTOCROSSLINKABLE SILANE DERIVATIVES

(75) Inventors: Richard Buchecker, Zürich (CH); Guy Marck, Schlierbach (FR); Hubert Seiberle, Weil am Rhein (DE)

(73) Assignee: Rolic AG, Basel (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/016,376

(22) Filed: Jan. 30, 1998

(30) Foreign Application Priority Data

Feb. 5, 1997 (EP) .................................. 97101757

(51) Int. Cl.$^7$ ................. B32B 9/00; C08G 77/00
(52) U.S. Cl. ............. 428/689; 528/10; 528/26; 528/27; 528/28; 528/32; 528/41; 528/42; 528/43; 528/271; 528/272; 528/395; 528/398; 528/401; 522/111; 522/148; 522/474; 522/477; 428/704
(58) Field of Search ............... 528/10, 271, 272, 528/395, 398, 401, 26, 27, 28, 32, 41, 42, 43; 522/111, 148; 525/474, 477; 428/689, 704

(56) References Cited

U.S. PATENT DOCUMENTS

| | | |
|---|---|---|
| 3,179,612 | 4/1965 | Plueddemann et al. . |
| 3,865,588 | 2/1975 | Ohto et al. . |
| 4,974,941 | * 12/1990 | Gibbons et al. ............... 350/349 |
| 5,539,074 | 7/1996 | Herr et al. . |
| 5,602,661 | 2/1997 | Schadt et al. . |

FOREIGN PATENT DOCUMENTS

| | | |
|---|---|---|
| A-2207495 | 8/1972 | (DE) . |
| A-611786 | 8/1994 | (EP) . |
| A-1337516 | 12/1963 | (FR) . |

OTHER PUBLICATIONS

Albanov et al., "NMR Study of (Aroyloxymethyl)Trifluorosilanes", J. Organometallic Chem., 244(1):5–16 (1983).
Horner et al., "Chemie an Starren Grenzflächen. 7. Ausgewählte Beispiele der Chemischen Grenzflächen–modifizierung von Aerosil", Z. Naturforsch., 42(5)643–660 (1987).
Kojima et al., "Preparation and Application of UV–curing Silicone Resins for Hard Coating Agents", Chemical Abstracts, 107(24):219187 (1987).
Creed et al., "Photochemical Crosslinking of Novel Polycinnamate Main–Chain Mesogens", MOL. CRYST. LIQ. CRYST., 155:57–71 (1988).
Tomita et al., "Command Surfaces 15[1]. Photoregulation of Liquid Crystal Alignment by Cinnamoyl Residues on a Silica Surface", LIQ. CRYST., 20(2):171–176 (1996).

* cited by examiner

Primary Examiner—Samuel A. Acquah
(74) Attorney, Agent, or Firm—Finnegan, Henderson, Farabow, Garrett, & Dunner L.L.P.

(57) ABSTRACT

The invention relates to novel crosslinkable, photoactive silane derivatives of the formula I

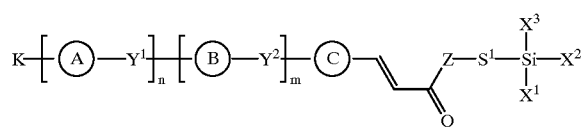

mixtures of silane derivatives of the formula I and mixtures of silane derivatives of the formula I with uncrosslinkable silane derivatives as usually used for silanizing inorganic, oxide-containing surfaces. The invention furthermore relates to the use of silane derivatives of the formula I and of mixtures which contain at least one silane derivative of the formula I as orientation layers for liquid crystals and for the production of unstructured or structured optical elements and multilayer systems.

22 Claims, No Drawings

PHOTOCROSSLINKABLE SILANE DERIVATIVES

BACKGROUND OF THE INVENTION

1. Field of the Invention

The invention relates to novel crosslinkable, photoactive silane derivatives with 3-arylacrylic esters and 3-arylacrylamides, and their use as orientation layers for liquid crystals and for the production of unstructured or structured optical elements and multilayer systems.

The orientation layer is particularly important in (electro-optical) liquid crystal devices. It serves for ensuring uniform and trouble-free orientation of the longitudinal axes of the molecules.

2. Description of the Prior Art

Uniaxially rubbed polymer orientation layers, such as, for example, polyimide, are usually used for orienting liquid crystal molecules in liquid crystal displays (LCDs). The direction of rubbing determines the orientation direction in this process. However, rubbing entails some serious disadvantages which may strongly influence the optical quality of liquid crystal displays. Thus, rubbing produces dust which may lead to optical defects in the display. At the same time, the polymer layer is electrostatically charged, which, for example in thin film transistor (TFT)-TN-LCDs, may result in the destruction of the thin film transistors underneath. For these reasons, the yield of optically satisfactory displays in LCD production has not been optimal to date.

A further disadvantage of rubbing is that it is not possible to produce structured orientation layers in a simple manner since the orientation direction cannot be varied locally during rubbing. Thus, mainly layers uniformly aligned over a large area can be produced by rubbing. However, structured orientation layers are of considerable interest in many areas of display technology and integrated optics. For example, the dependency of the angle of view of twisted nematic (TN) LCDs can thus be improved.

Orientation layers in which the orientation direction can be predetermined by exposure to polarized light have been known for some time. The problems inherent in rubbing can thus be overcome. In addition, it is possible to specify the orientation direction differently from region to region and hence to structure the orientation layer.

One possibility for the structured orientation of liquid crystals utilizes the isomerizability of certain dye molecules for inducing a preferred direction photochemically by exposure to polarized light of suitable wavelength. This is achieved, for example, by mixing a dye with an orientation polymer and then exposing said dye to polarized light. Such a guest/host system is described, for example, in U.S. Pat. No. 4,974,941. In this system, azobenzenes are mixed into polyimide orientation layers and then exposed to polarized light. Liquid crystals which are in contact with the surface of a layer exposed in this manner are oriented according to this preferred direction. This orientation process is reversible, i.e. the already established direction of orientation can be rotated again by further exposure of the layer to light having a second polarization direction. Since this reorientation process can be repeated as often as desired, orientation layers of this type are less suitable for use in LCDs.

A further possibility for producing highly resolved orientation patterns in liquid crystalline layers is described in Jpn. J. Appl. Phys. Vol. 31 (1992), 2155. In this process, the dimerization of polymer-bound photoreactive cinnamic acid groups, induced by exposure to linearly polarized light, is utilized for the structured orientation of liquid crystals. In contrast to the reversible orientation process described above, an anisotropic polymer network is established in the case of the photostructurable orientation layers described in Jpn. J. Appl. Phys. Vol. 31 (1992), 2155. These photo-oriented polymer networks can be used wherever structured or unstructured liquid crystal orientation layers are required. Apart from in LCDs, such orientation layers can also be used, for example, for the production of so-called hybrid layers, as exemplified in European Patent Applications EP-A-0 611 981, EP-A-0 689 084 and EP-A-0 689 065 and in Swiss Patent Application No. 2036/95. With these hybrid layers of photostructured orientation polymers and crosslinkable low molecular weight liquid crystals, it is possible to realize optical elements, such as, for example, nonabsorptive color filters, linear and circular polarizers, optical retardation layers, etc.

EP-A-611,786 describes cinnamic acid polymers which are suitable in principle for the production of such anisotropically crosslinked, photostructured orientation layers for liquid crystals. These crosslinkable cinnamic acid derivatives are in principle linked to the polymer main chain via the carboxyl function of the cinnamic acid (phenylacrylic acid) and a spacer. However, the photopolymers of this type which have been used to date have a number of serious disadvantages. Thus, for example, photochemical competing reactions adversely affect the orientability. In addition, the known cinnamic acid polymers have insufficient photochemical long-term stability. For example, prolonged exposure of a prefabricated orientation layer to UV light leads to the destruction of the orientation originally present. Multiple exposures in which an existing orientation layer having a predetermined recorded pattern is exposed again in order to orient the still unexposed parts in another direction can be carried out only if the previously exposed parts are covered by a mask. Otherwise, the already oriented parts of the layer may lose some or all of their structure as a result of photochemical secondary reactions.

A further disadvantage of the cinnamic acid polymers used to date is that there is no tilt angle in the case of the orientation surfaces comprising these materials, which surfaces are produced by simple exposure to polarized light. Particularly for use in LCDs, however, a tilt angle must also be provided by the orientation layer in addition to the orientation direction.

In the above-mentioned uniaxially rubbed polymer orientation layers, this tilt angle is already generated in the rubbing process on the polymer surface. If a liquid crystal is brought into contact with such a surface, the liquid crystal molecules are not parallel but inclined to the surface and the tilt angle is thus transmitted to the liquid crystal. The magnitude of the tilt angle is determined both by rubbing parameters, such as, for example, feed rate and pressure, and by the chemical structure of the polymer. For the production of liquid crystal displays, tilt angles between 1° and 15° are required, depending on the type. The larger tilt angles are required in particular for supertwisted nematic (STN) LCDs, in order to avoid the formation of so-called fingerprint textures. In TN and TFT-TN-LCDs, the direction of rotation and the tilting direction are defined by the tilt angle, with the result that "reverse twist" and "reverse tilt" phenomena are prevented. While reverse twist in the unswitched state results in regions with an incorrect direction of rotation, which is manifested visually in a mottled appearance of the display, reverse tilt is optically very troublesome, especially on switching the LCD by tilting the liquid crystals in different directions. Reverse twist can be prevented by doping the liquid crystal mixture with a chiral dopant of suitable direction of rotation. For suppressing reverse tilt, however, there is to date no alternative possibility to the use of orientation layers with a tilt angle.

Recently, cinnamic esters which are not bonded, as described above, to a polymer skeleton but are linked by the spacers to a trialkoxysilane group were reported in Liq. Cryst. 20, 171 (1996). Here, the trialkoxysilane group serves for anchoring the cinnamic acid unit to the substrate as a carrier, for example of glass. The spacer which links the trialkoxysilane group to the cinnamic ester is always attached in the 2-position (ortho position) of the cinnamic ester. For the production of the orientation layer, the trialkoxysilanes are first applied to the glass carrier from a solution. The orientation is then effected by exposure to linearly polarized light of 259 nm wavelength. The ability of the layer prepared in this manner to orient liquid crystal is ascribed to reversible Z/E isomerization. If, on the other hand, the cinnamic acid molecules are exposed at 330 nm, they are crosslinked. Orientability is lost in proportion to the degree of crosslinking.

The orientation layers produced in this manner have the same disadvantages as the cinnamic acid polymers described further above. They too have insufficient photochemical and thermal stability since the Z/E isomerization is reversible and therefore lead to problems associated with reorientation on multiple exposure. In addition, they too lack the ability to induce tilt angles.

SUMMARY OF THE INVENTION

It was therefore the object of the invention to produce photoreactive silanes which do not have the above disadvantages of the cinnamic acid polymers and silanes used to date, i.e. the lack of photochemical long-term stability and especially the lack of a tilt angle after exposure to polarized light, and thus capable of producing stable, highly resolved orientation patterns.

Surprisingly, it has now been found that silanes which are linked by a spacer to the carbonyl or carboxyl function of 3-arylacrylic acid derivatives as a photoreactive unit fulfil this condition and are very suitable as orientation layers for liquid crystals. The crosslinking of these compounds with linearly polarized light leads to significantly higher photochemical stability of the orientation layer and at the same time to excellent orientation of liquid crystals, which is distinguished, for example, by very good contrast. In addition, tilt angles are generated on exposure to linearly polarized light.

The present invention relates to silanes of the general formula I:

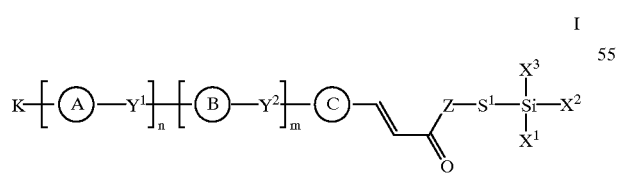

I in which

X$^1$, X$^2$ and X$^3$ denote alkyl, alkoxy or halogen, but at least one of these radicals is either alkoxy or halogen;

S$^1$ denotes a spacer unit, such as a straight-chain or branched alkylene group —(CH$_2$)$_r$— which is optionally mono- or polysubstituted by fluorine, chlorine or cyano, or denotes a chain of the formula —(CH$_2$)$_r$—L—(CH$_2$)$_s$—, in which L denotes a single bond or linking functional groups, such as O, COO, OOC, NR$^1$, NR$^1$—CO—, CO—NR$^1$, NR$^1$—COO, OCO—NR$^1$, NR$^1$—CO—NR$^1$, —CH=CH— or —C≡C—, R$^1$ denotes hydrogen or lower alkyl and r and s each represent an integer from 1 to 20, with the proviso that r+s is ≦25;

Ring A denotes unsubstituted or fluorine-, chlorine-, cyano-, alkyl- or alkoxy-substituted phenylene, pyrid-2,5-diyl, pyrimidin-2,5-diyl, 1,3-dioxane-2,5-diyl, cyclohexane-1,4-diyl, piperidin-1,4-diyl or piperazin-1,4-diyl, it being possible for the alkyl and/or the alkoxy substituent to be mono- or polysubstituted by fluorine;

Ring B denotes unsubstituted or fluorine-, chlorine-, cyano-, alkyl- or alkoxy-substituted phenylene, pyrid-2,5-diyl, pyrimidin-2,5-diyl, 1,4- or 2,6-naphthylene, 1,3-dioxane-2,5-diyl or cyclohexane-1,4-diyl, it being possible for the alkyl and/or the alkoxy substituent to be mono- or polysubstituted by fluorine;

K is hydrogen, fluorine, chlorine, cyano, nitro or a straight-chain or branched alkyl, alkoxy, alkyl-COO, alkyl-CO—NR$^2$ or alkyl-OCO group having 1 to 20 carbon atoms which is optionally substituted by fluorine, chlorine, cyano or nitro and in which optionally one CH$_2$ group or a plurality of non-neighboring CH$_2$ groups may be replaced by O, CH=CH or C≡C and in which R$^2$ denotes hydrogen or lower alkyl;

Y$^1$ and Y$^2$, independently of one another, denote a single covalent bond, —(CH$_2$)$_t$—, —O—, —CO—, —CO—O—, —O—OC—, —NR$^3$—, —CO—NR$^3$—, —R$^3$N—CO—, —(CH$_2$)$_u$—O—, —O—(CH$_2$)$_u$—, —(CH$_2$)$_u$—NR$^3$— or —NR$^3$—(CH$_2$)$_u$—, in which R$^3$ denotes hydrogen or lower alkyl;

t denotes an integer from 1 to 4;

u denotes an integer from 1 to 3;

m and n, independently of one another, denote 0 or 1;

Ring C denotes unsubstituted or fluorine-, chlorine-, cyano-, alkyl- or alkoxy-substituted phenylene, pyrimidin-2,5- or 3,5-diyl, pyrid-2,5- or -2,4-diyl or -2,6-diyl, 2,5-thiophenylene, 2,5-furanylene, 1,4- or 2,6-naphthylene, it being possible for the alkyl and/or the alkoxy substituent to be mono- or polysubstituted by fluorine;

Z denotes —O— or —NR$^4$— and R$^4$ denotes hydrogen or lower alkyl.

DETAILED DESCRIPTION

The photocrosslinkable silane derivatives of the formula I according to the invention can be used individually or in mixtures for the formation of orientation layers. In addition to one or more compounds of the formula I, suitable mixtures optionally also contain other, uncrosslinkable silane derivatives, as usually used for silanizing inorganic, oxide-containing surfaces. Such uncrosslinkable silane derivatives are, for example, compounds of the general formula II

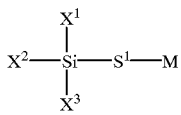

in which $X^1$, $X^2$, $X^3$ and $S^1$ have the meaning stated under formula I and M denotes a mesogenic radical, lower alkyl, lower alkyl mono- or polysubstituted by fluorine, lower alkoxy or lower alkoxy mono- or polysubstituted by fluorine.

Such mixtures which contain at least one photocrosslinkable silane derivative of the general formula I are likewise the subject of the present invention.

In the context of the present invention, the term "mesogenic radical" means a group corresponding to the general formula III

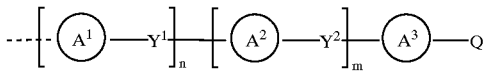

in which the rings $A^1$, $A^2$ and $A^3$ denote unsubstituted or fluorine-, chlorine-, cyano-, alkyl- or alkoxy-substituted phenylene, pyrid-2,5-diyl, pyrimidin-2,5-diyl, 2,6-naphthylene, 1,3-dioxane-2,5-diyl or cyclohexane-1,4-diyl, it being possible for the alkyl and/or the alkoxy substituent to be mono- or polysubstituted by fluorine, and not more than one of the rings differing from phenylene or cyclohexylene;

Q denotes lower alkyl or alkoxy in which one or more hydrogen atoms may be replaced by fluorine, or denotes fluorine, chlorine, cyano or nitro;

n, m, $Y^1$ and $Y^2$ have the meaning stated in the formula I.

Preferably, M in compounds of the formula II denotes lower alkyl or a lower alkoxy or a mesogenic radical of the formula III in which n represents 0 and m represents 0 or 1 and the rings $A^1$, $A^2$ and $A^3$ denote phenylene or cyclohexylene; $Y^1$ and $Y^2$ denote a single covalent bond, —CH$_2$CH$_2$—, —O—, —CH$_2$—O—, —O—CH$_2$—, —CO—O— or —O—OC— and Q denotes optionally fluorine-substituted lower alkyl or lower alkoxy, fluorine, chlorine or cyano.

Compounds of the formula II in which M denotes lower alkyl, lower alkoxy or a radical of the formula III in which m and n represent 0 and Q is optionally fluorine-substituted lower alkyl or lower alkoxy are very particularly preferred.

The proportion of silane derivatives in the mixtures according to the invention which do not correspond to a structure of the formula I is less than or equal to 50%, preferably less than or equal to 30%, but in particular less than or equal to 15%.

The present invention also relates to the use of the silane derivatives of the formula I according to the invention or the use of mixtures of silane derivatives of the formulae I and II for the production of orientation layers for liquid crystals, and to their use in optical components, in particular for the production of hybrid layer elements.

The term "lower alkyl" alone or in combination, such as "lower alkoxy", designates straight-chain and branched saturated hydrocarbon radicals having 1 to 6, preferably having 1 to 3, carbon atoms, such as methyl, ethyl, propyl or isopropyl and the like.

The term "alkyl" alone or in combination, such as "alkoxy", designates straight-chain or branched saturated hydrocarbon radicals having up to 30 carbon atoms.

In the context of the present invention, preferred "spacer units" are a straight-chain or branched alkylene group, represented by —(CH$_2$)$_r$—, as well as —(CH$_2$)$_r$—O—(CH$_2$)$_s$—, —(CH$_2$)$_r$—COO—(CH$_2$)$_s$—, —(CH$_2$)$_r$—OOC—(CH$_2$)$_s$—, —(CH$_2$)$_r$—NR$^1$—CO—(CH$_2$)$_s$— or —(CH$_2$)$_r$—NR$^1$—COO—(CH$_2$)$_s$—, in which r and s are each an integer from 1 to 20, but in particular 2 to 12, with the proviso that r+s≦20, in particular ≦15, and in which $R^1$ denotes hydrogen or lower alkyl.

Examples of preferred "spacer units" are 1,2-ethylene, 1,3-propylene, 1,4-butylene, 1,5-pentylene, 1,6-hexylene, 1,7-heptylene, 1,8-octylene, 1,9-nonylene, 1,10-decylene, 1,11-undecylene, 1,12-dodecylene, 1,3-butylene, 3-methyl-1,3-butylene, 3-propyleneoxy-6-hexylene, 3-propylenecarbamoyloxy-6-hexylene, 3-propylenecarbonyloxy-6-hexylene, 3-propyleneoxycarbonyl-6-hexylene, 3-propylenecarbonylamino-6-hexylene, propylenecarbamoylhexylene and the like.

Particularly preferred "spacer units" are a straight-chain alkylene group represented by —(CH$_2$)$_r$—, as well as —(CH$_2$)$_r$—NH—CO—(CH$_2$)— or —(CH$_2$)$_r$—NH—COO—(CH$_2$)$_s$—, in which r and s are each an integer from 2 to 12 and the sum r+s is ≦15.

In the context of the present invention, the term "unsubstituted or optionally fluorine-, chlorine-, cyano-, alkyl- or alkoxy-substituted phenylene" comprises 1,3- or 1,4-phenylene which is unsubstituted or mono- or polysubstituted by fluorine, chlorine, cyano, alkyl or alkoxy, preferably by fluorine, methyl, ethyl, propyl, butyl, methoxy, ethoxy, propoxy, butoxy or cyano.

Examples of preferred phenylene radicals are 1,3- and 1,4-phenylene, 4- and 5-methyl-1,3-phenylene, 4- and 5-methoxy-1,3-phenylene, 4- and 5-ethyl-1,3-phenylene, 4- and 5-ethoxy-1,3-phenylene, 2- and 3-methyl-1,4-phenylene, 2- and 3-ethyl-1,5-phenylene, 2- and 3-propyl-1,4-phenylene, 2- and 3-butyl-1,4-phenylene, 2- and 3-methoxy-1,4-phenylene, 2- and 3-ethoxy-1,4-phenylene, 2- and 3-propoxy-1,4-phenylene, 2- and 3-butoxy-1,4-phenylene, 2,3-, 2,6- and 3,5-dimethyl-1,4-phenylene, 2,6- and 3,5-dimethoxy-1,4-phenylene, 2- and 3-fluoro-1,4-phenylene, 2,3-, 2,6- and 3,5-difluoro-1,4-phenylene, 2- and 3-chloro-1,4-phenylene, 2,3-, 2,6- and 3,5-dichloro-1,4-phenylene, 2- and 3-cyano-1,4-phenylene, and the like.

In the context of the present invention, preferred substituents K are hydrogen, fluorine, chlorine, cyano, nitro and alkyl, alkoxy, alkyl-COO, alkyl-CONR$^2$ or alkyl-OCO groups in which the alkyl radical is straight-chain or branched and optionally at least monosubstituted by fluorine, the number of carbon atoms is 1–15 and $R^2$ represents hydrogen or lower alkyl.

Preferred silane derivatives of the formula I are those in which $X^1$, $X^2$, $X^3$, $S^1$, K, m and n have the meaning stated under formula I and Ring A denotes unsubstituted or fluorine-, chlorine-, cyano-, alkyl- or alkoxy-substituted phenylene, pyrid-2,5-diyl, pyrimidin-2,5-diyl or cyclohexane-1,4-diyl, it being possible for the alkyl and/or the alkoxy substituent to be mono- or polysubstituted by fluorine;

Ring B denotes unsubstituted or fluorine-, chlorine-, cyano-, alkyl- or alkoxy-substituted phenylene, pyrid-2,5-diyl, pyrimidin-2,5-diyl, 1,4- or 2,6-naphthylene or cyclohexane-1,4-diyl, it being possible for the alkyl and/or the alkoxy substituent to be mono- or polysubstituted by fluorine;

$Y^1$ and $Y^2$, independently of one another, denote a single covalent bond, —CH$_2$CH$_2$—, —O—, —CH$_2$—O—, —O—CH$_2$—, —CO—O— or —O—OC—;

Ring C denotes unsubstituted or fluorine-, chlorine-, cyano-, alkyl- or alkoxy-substituted 1,3- or 1,4-phenylene, pyrimidin-2,5-diyl, pyrid-2,5-diyl, 2,5-furanylene or 1,4- or 2,6-naphthylene, it being possible for the alkyl and/or the alkoxy substituent to be mono- or polysubstituted by fluorine;

Z denotes —O—.

Particularly preferred silane derivatives of the formula I are those in which $X^1$, $X^2$, $X^3$, $S^1$, K and m have the meaning stated under formula I and n denotes 0;

Ring B denotes unsubstituted or fluorine-, chlorine-, cyano-, alkyl- or alkoxy-substituted phenylene, pyrid-2,5-diyl, pyrimidin-2,5-diyl or cyclohexane-1,4-diyl, it being possible for the alkyl and/or the alkoxy substituent to be mono- or polysubstituted by fluorine;

$Y^2$ denotes a single covalent bond, —CO—O— or —CH$_2$—O—;

Ring C denotes unsubstituted or fluorine-, chlorine-, cyano-, alkyl or alkoxy- substituted 1,3- or 1,4-phenylene, or 1,4- or 2,6-naphthylene, it being possible for the alkyl and/or the alkoxy substituent to be mono- or polysubstituted by fluorine;

Z denotes —O—.

The silane derivatives of the formula I are distinguished by the fact that they are easily obtainable. The methods for the preparation are known per se to a person skilled in the art. Thus, for example, precursors of the compounds of the formula I which have a terminal double bond instead of the silane group at the end of the spacer $S^1$ can be subjected to a hydrosilylation reaction with commercial silanes of the formula $X^1X^2X^3$SiH to give the compounds of the formula I. A further method of preparation consists in reacting a silane of the formula $X^1X^2X^3$Si—(CH$_2$)$_r$—N=C=O with a hydroxy or amino compound in which the hydroxyl or the amino group is present at the desired linkage point in the spacer. This gives rise to those compounds of the formula I which have an N—CO—O or N—CO—N group in the spacer. By reacting the above-mentioned hydroxy or amino compounds with silanes of the formula $X^1X^2X^3$Si—(CH$_2$)$_r$—Br, it is possible, on the other hand, to prepare those compounds of the formula I which have an ether function or an alkylamino group in the spacer. By reacting silanes of the formula $X^1X^2X^3$Si—(CH$_2$)$_r$—NHR$^1$ with an acid chloride, it is possible to prepare those silanes of the formula I which have an NR$^1$CO group in the spacer. By reacting the acid chlorides of the cinnamic acid intermediate with silanes of the formula $X^1X^2X^3$Si—(CH$_2$)$_r$—NHR, there is a further possibility, in addition to the hydrosilylation of the corresponding alkenylamides, for the preparation of cinnamides of the formula I in which Z represents NR$^4$ and Si represents —CH$_2$)$_r$—. Such methods of preparation have been described with reference to analogous examples in U.S. Pat. No. 4,918,200 and U.S. Pat. No. 4,861,906.

The silane intermediates are for the most part commercially available or can easily be modified from commercial silane building blocks. Some of the cinnamic acids are likewise commercially available while others can be obtained by methods known from the literature, such as, for example, the Knoevenagel or the Wittig reaction, from commercial aldehydes or from cyano compounds, by prior reduction to the corresponding aldehydes. The cinnamic esters or amides can then be prepared from the cinnamic acids by known esterification methods.

For the production of the orientation layers, the silane derivatives or mixtures according to the invention must first be applied to a carrier. The silane groups are subsequently bonded as coupling units to the carrier and form extremely thin, often monomolecular layers. Such silanizations of different, generally inorganic oxides are widely used in practice and are quite familiar to a person skilled in the art. Examples of known carrier materials are aluminum oxide, titanium dioxide, silicon dioxide (glass or quartz) or mixed oxides, such as, for example, indium tin oxide (ITO). In the applications according to the invention for optical or electro-optical devices, glass or optionally a carrier coated with an electrode (for example a glass sheet coated with indium tin oxide (ITO)) are particularly important as carrier materials. For the application, the silane derivatives are used predominantly as solutions in an inert solvent. Depending on the reactivity of the silane group, a large number of different solvents may be used, such as, for example, benzene, toluene, hexane, etc., or, in the case of the less reactive alkoxysilanes, also alcohols, such as methanol, ethanol and the like. The subsequent coating can be carried out, for example, by immersing the cleaned carrier in the solution, by spin coating or by other coating techniques. After volatilization of the solvent from the carrier layer, the silane group is coupled to the carrier, generally by heating the impregnated carrier, depending on the reactivity. The unbound silane fractions can then be washed out with solvents.

The layers which were produced from silane derivatives of the formula I or from mixtures containing silane derivatives of the formula I in this or an analogous manner can be dimerized by exposure to linearly polarized light. By spatially selective irradiation of the molecular units of the formula I coupled to the carrier, very specific regions of a surface can now be oriented and at the same time also stabilized by the dimerization.

Thus, for the production of orientation layers in selected areas, the regions to be oriented can be exposed, for example, to a high-pressure mercury lamp, a xenon lamp or a pulsed UV laser with the use of a polarizer and optionally a mask for reproducing structures. The exposure time is dependent on the power of the individual lamps and may vary from a few minutes to several hours. However, the dimerization can also be effected by irradiation of the homogeneous layer with the use of filters which, for example, let through only the radiation suitable for the crosslinking reaction.

The photocrosslinkable silane derivatives of the formula I according to the invention are further illustrated by the following Examples 1–5.

The production of a photocrosslinkable layer is illustrated by Example 6.

Examples 7 and 8 illustrate the production of an orientation layer for liquid crystals.

EXAMPLE 1

6-(3-Triethoxysilanylpropylcarbamoyloxy)hexyl (E)-3,4-dimethoxycinnamate

A mixture of 0.45 g of 6-hydroxyhexyl (E)-3,4-dimethoxycinnamate, 20 ml of methylene chloride, 0.36 ml of 3-triethoxysilanylpropyl isocyanate and 0.009 ml of dibutyltin dilaurate was refluxed for 19 hours. Thereafter, the reaction solution was evaporated down and the residue was purified by chromatography over 150 g of silica gel using 3:1 toluene/ethyl acetate. This gave 0.470 g of 6-(3-triethoxysilanylpropylcarbamoyloxy)hexyl 3,4-dimethoxycinnamate, lmax. (CH$_2$Cl$_2$): 322 nm (e=19027).

The 6-hydroxyhexyl (E)-3,4-dimethoxycinnamate used as starting material was prepared as follows:

6-Hydroxyhexyl (E)-3,4-dimethoxycinnamate

A solution consisting of 0.72 ml of 1,8-diazabicyclo [5.4.0]undec-7-ene (1.5-5) and 5 ml of dimethylformamide was added dropwise to a solution of 1.0 g of (E)-3,4-dimethoxycinnamic acid in 10 ml of dimethylformamide in the course of 10 minutes at room temperature. The reaction mixture was then heated to 80° C., 0.18 g of tetrabutylammonium iodide and 0.71 ml of 6-chlorohexanol were then added in succession and the reaction was then allowed to continue for 19 hours. Thereafter, the reaction mixture was cooled to room temperature and was partitioned between diethyl ether and 1 N hydrochloric acid and the organic phase was washed several times with saturated sodium chloride solution. The organic phase was then dried over magnesium sulfate, filtered and evaporated down. Chromatography of the residue over 150 g of silica gel using 3:2 toluene/ethyl acetate gave 1.35 g of 6-hydroxyhexyl (E)-3, 4-dimethoxycinnamate.

The following silanes were synthesized in an analogous manner:

6-(3-triethoxysilanylpropylcarbamoyloxy)hexyl (E)-2-methoxycinnamate;
6-(3-triethoxysilanylpropylcarbamoyloxy)hexyl (E)-3-methoxycinnamate;
6-(3-triethoxysilanylpropylcarbamoyloxy)hexyl (E)-3-octyloxycinnamate;
6-(3-triethoxysilanylpropylcarbamoyloxy)hexyl (E)-4-methoxycinnamate;
6-(3-triethoxysilanylpropylcarbamoyloxy)hexyl (E)-4-ethoxycinnamate;
6-(3-triethoxysilanylpropylcarbamoyloxy)hexyl (E)-4-propoxycinnamate;
6-(3-triethoxysilanylpropylcarbamoyloxy)hexyl (E)-4-butoxycinnamate;
6-(3-triethoxysilanylpropylcarbamoyloxy)hexyl (E)-4-pentyloxycinnamate;
6-(3-triethoxysilanylpropylcarbamoyloxy)hexyl (E)-4-hexyloxycinnamate;
6-(3-triethoxysilanylpropylcarbamoyloxy)hexyl (E)-4-dodecyloxycinnamate;
6-(3-triethoxysilanylpropylcarbamoyloxy)hexyl (E)-3-fluorocinnamate;
6-(3-triethoxysilanylpropylcarbamoyloxy)hexyl (E)-4-fluorocinnamate;
6-(3-triethoxysilanylpropylcarbamoyloxy)hexyl (E)-3-chlorocinnamate;
6-(3-triethoxysilanylpropylcarbamoyloxy)hexyl (E)-4-chlorocinnamate;
6-(3-triethoxysilanylpropylcarbamoyloxy)hexyl (E)-4-trifluoromethoxycinnamate;
6-(3-triethoxysilanylpropylcarbamoyloxy)hexyl (E)-4-acetamidocinnamate;
6-(3-triethoxysilanylpropylcarbamoyloxy)hexyl (E)-4-pentanoylaminocinnamate;
6-(3-triethoxysilanylpropylcarbamoyloxy)hexyl (E)-4-decanoylaminocinnamate;
6-(3-triethoxysilanylpropylcarbamoyloxy)hexyl (E)-3,5-dimethoxycinnamate;
6-(3-triethoxysilanylpropylcarbamoyloxy)hexyl (E)-2,5-dimethoxycinnamate;
6-(3-triethoxysilanylpropylcarbamoyloxy)hexyl (E)-3-methoxy-4-propoxycinnamate;
6-(3-triethoxysilanylpropylcarbamoyloxy)hexyl (E)-3-methoxy-4-octyloxycinnamate;
6-(3-triethoxysilanylpropylcarbamoyloxy)hexyl (E)-3-decyloxy-4-methoxycinnamate;
6- (3-triethoxysilanylpropylcarbamoyloxy)hexyl (E)-3-fluoro-4-methoxycinnamate;
6-(3-triethoxysilanylpropylcarbamoyloxy)hexyl (E)-3-chloro-4-methoxycinnamate;
6-(3-triethoxysilanylpropylcarbamoyloxy)hexyl (E)-3-propyl-4-methoxycinnamate;
6-(3-triethoxysilanylpropylcarbamoyloxy)hexyl (E)-3,4,5-trimethoxycinnamate;
6-(3-triethoxysilanylpropylcarbamoyloxy)hexyl (E)-3,4-difluorocinnamate;
6-(3-triethoxysilanylpropylcarbamoyloxy)hexyl (E)-2,3-difluorocinnamate;
6-(3-triethoxysilanylpropylcarbamoyloxy)hexyl (E)-3,4,5-trifluorocinnamate;
6-(3-triethoxysilanylpropylcarbamoyloxy)hexyl (E)-3-fluoro-4-chlorocinnamate;
6-(3-triethoxysilanylpropylcarbamoyloxy)hexyl (E)-3-ethoxy-4-acetamidocinnamate;
6-(3-triethoxysilanylpropylcarbamoyloxy)hexyl (E)-4-(4-methoxybenzoyloxy)cinnamate;
6-(3-triethoxysilanylpropylcarbamoyloxy)hexyl (E)-3-methoxy-4-(4-methoxybenzoyloxy)cinnamate;
6-(3-triethoxysilanylpropylcarbamoyloxy)hexyl (E)-4-(3,4-dimethoxybenzoyloxy)cinnamate;
6-(3-triethoxysilanylpropylcarbamoyloxy)hexyl (E)-3-methoxy-4-(3,4-dimethoxybenzoyloxy)cinnamate;
6-(3-triethoxysilanylpropylcarbamoyloxy)hexyl (E)-3-ethoxy-4-(3,4-dimethoxybenzoyloxy)cinnamate;
6-(3-triethoxysilanylpropylcarbamoyloxy)hexyl (E)-4-(4-methoxyphenyl)cinnamate;
6-(3-triethoxysilanylpropylcarbamoyloxy)hexyl (E)-4-(3,4-dimethoxyphenyl)cinnamate;
6-(3-triethoxysilanylpropylcarbamoyloxy)hexyl (E)-4-(4-ethylphenyl)cinnamate;
6-(3-triethoxysilanylpropylcarbamoyloxy)hexyl (E)-4-(4-hexylphenyl)cinnamate;
6-(3-triethoxysilanylpropylcarbamoyloxy)hexyl (E)-4-(trans-4-pentylcyclohexyl)cinnamate;
6-(3-triethoxysilanylpropylcarbamoyloxy)hexyl (E)-4-(cis-4-pentylcyclohexyl)cinnamate;
6-(3-triethoxysilanylpropylcarbamoyloxy)hexyl (E)-4-[(trans-4-pentylcyclohexyl)methoxy]cinnamate;
6-(3-triethoxysilanylpropylcarbamoyloxy)hexyl (E)-4-[(cis-4-pentylcyclohexyl)methoxy]cinnamate;
6-(3-triethoxysilanylpropylcarbamoyloxy)hexyl (E)-4-[4-(trans-4-pentylcyclohexyl)phenyl]cinnamate;
6-(3-triethoxysilanylpropylcarbamoyloxy)hexyl (E)-4-[4-(cis-4-pentylcyclohexyl)phenyl]cinnamate.

EXAMPLE 2

6-Triethoxysilanylhexyl (E)-3,4-dimethoxycinnamate

A mixture of 0.50 g of hex-5-enyl 3,4-dimethoxycinnamate, 1.0 ml of toluene, 2.9 ml of triethoxysilane and 0.02 ml of a solution of 134 mg of hexachloro (IV) platinic acid hexahydrate in 10 ml of isopropanol is allowed to react overnight at 40° C. The reaction mixture is then cooled to room temperature and filtered over a silica gel pad and the filtrate is completely evaporated down. Chromatography of the residue over silica gel gives 6-triethoxysilanylhexyl 3,4-dimethoxycinnamate.

The hex-5-enyl 3,4-dimethoxycinnamate used as a starting material is prepared as follows:

Hex-5-enyl 3,4-dimethoxycinnamate

A solution consisting of 0.72 ml of 1,8-diazabicyclo [5.4.0]undec-7-ene (1.5–5) in 5 ml of dimethylformamide is added dropwise to a mixture of 1.0 g of 3,4-dimethoxycinnamic acid and 10 ml of dimethylformamide in the course of 10 minutes at room temperature. The reaction mixture is heated to 80° C., a solution of 0.71 ml of 6-bromohexene in 5 ml of dimethylformamide is then added dropwise in the course of 50 minutes and the reaction is allowed to continue for 1 hour at 80° C. The reaction mixture is then cooled to room temperature and partitioned between diethyl ether and 1 N hydrochloric acid and the organic phase is washed several times with saturated sodium chloride solution. Thereafter, the organic phase is dried over magnesium sulfate and filtered and the filtrate is evaporated down. Chromatography of the residue over silica gel gives hex-6-enyl 3,4-dimethoxycinnamate.

The following silane derivatives can be prepared in an analogous manner:

6-triethoxysilanylhexyl (E)-2-methoxycinnamate;
8-triethoxysilanyloctyl (E)-3-methoxycinnamate;
6-triethoxysilanylhexyl (E)-3octyloxycinnamate;
8-triethoxysilanyloctyl (E)-4-methoxycinnamate;
8-triethoxysilanyloctyl (E)-4-ethoxycinnamate;
8-triethoxysilanyloctyl (E)-4-propoxycinnamate;
6-triethoxysilanylhexyl (E)-4-butoxycinnamate;
8-triethoxysilanyloctyl (E)-4-pentyloxycinnamate;
8-triethoxysilanyloctyl (E)-4-hexyloxycinnamate;
6-triethoxysilanylhexyl (E)-4-dodecyloxycinnamate;
6-triethoxysilanylhexyl (E)-3-fluorocinnamate;
6-triethoxysilanylhexyl (E)-4-fluorocinnamate;
6-triethoxysilanylhexyl (E)-3-chlorocinnamate;
6-triethoxysilanylhexyl (E)-4-chlorocinnamate;
8-triethoxysilanyloctyl (E)-4-trifluoromethoxycinnamate;
6-triethoxysilanylhexyl (E)-4-acetamidocinnamate;
8-triethoxysilanyloctyl (E)-4-acetamidocinnamate;
6-triethoxysilanylhexyl (E)-4-pentanoylaminocinnamate;
6-triethoxysilanylhexyl (E)-4-decanoylaminocinnamate;
5-triethoxysilanylpentyl (E)-3,4-dimethoxycinnamate;
7-triethoxysilanylheptyl (E)-3,4-dimethoxycinnamate;
8-triethoxysilanyloctyl (E)-3,4-dimethoxycinnamate;
9-triethoxysilanylnonyl (E)-3,4-dimethoxycinnamate;
10-triethoxysilanyldecyl (E)-3,4-dimethoxycinnamate;
11-triethoxysilanylundecyl (E)-3,4-dimethoxycinnamate;
12-triethoxysilanyldodecyl (E)-3,4-dimethoxycinnamate;
6-triethoxysilanylhexyl (E)-3,5-dimethoxycinnamate;
6-triethoxysilanylhexyl (E)-2,5-dimethoxycinnamate;
8-triethoxysilanyloctyl (E)-3-methoxy-4-propoxycinnamate;
6-triethoxysilanylhexyl (E)-3-methoxy-4-octyloxycinnamate;
6-triethoxysilanylhexyl (E)-3-decyloxy-4-methoxycinnamate;
6-triethoxysilanylhexyl (E)-3-fluoro-4-methoxycinnamate;
8-triethoxysilanyloctyl (E)-3-chloro-4-methoxycinnamate;
8-triethoxysilanyloctyl (E)-3-propyl-4-methoxycinnamate;
6-triethoxysilanylhexyl (E)-3,4,5-trimethoxycinnamate;
8-triethoxysilanyloctyl (E)-3,4-difluorocinnamate;
8-triethoxysilanyloctyl (E)-2,3-difluorocinnamate;
8-triethoxysilanyloctyl (E)-3,4,5-trifluorocinnamate;
6-triethoxysilanylhexyl (E)-3-fluoro-4-chlorocinnamate;
6-triethoxysilanylhexyl (E)-3-ethoxy-4-acetamidocinnamate;
6-triethoxysilanylhexyl (E)-4-(4-methoxybenzoyloxy)cinnamate;
6-triethoxysilanylhexyl (E)-3-methoxy-4-(4-methoxybenzoyloxy)cinnamate;
6-triethoxysilanylhexyl (E)-4-(3,4-dimethoxybenzoyloxy)cinnamate;
6-triethoxysilanylhexyl (E)-3-methoxy-4-(3,4-dimethoxybenzoyloxy)cinnamate;
6-triethoxysilanylhexyl (E)-3-ethoxy-4-(3,4-dimethoxybenzoyloxy)cinnamate.

EXAMPLE 3

6-Triethoxysilanylhexyl (E)-4-[(trans-4-heptylcyclohexyl)methoxy]cinnamate

The compound is prepared analogously to Example 2 by esterification of (E)-4-[(trans-4-heptylcyclohexyl)methoxy]cinnamic acid with 6-bromohexene and subsequent reaction of the resulting hex-5-enyl (E)-4-[(trans-4-heptylcyclohexyl)methoxy]cinnamate with triethoxysilane.

The (E)-4-[(trans-4-heptylcyclohexyl)methoxy]cinnamic acid used as a starting material is prepared by the following process:

4-[(trans-4-heptylcyclohexyl)methoxy]benzaldehyde 38.5 ml of a diisobutylaluminum hydride solution (20% in toluene) are added dropwise to a suspension of 10.4 g of 4-[(trans-4-heptylcyclohexyl)methoxy]benzo-nitrile, prepared according to Mol. Cryst. Liq. Cryst. 53, 147 (1979), in 150 ml of toluene in the course of 10 minutes at 0° C. The reaction mixture is then slowly warmed up to room temperature and is allowed to react for a further 3.5 hours. Thereafter, 1 N hydrochloric acid is slowly added dropwise, stirring is carried out for 1 hour and the reaction mixture is then partitioned between water and methylene chloride. The organic phase is then washed several times with water, dried over magnesium sulfate, filtered and evaporated down. Crystallization from ethyl acetate/methylene chloride gives 4-[(trans-4-heptylcyclohexyl)methoxy]benzaldehyde.

Methyl 4-[(trans-4-heptylcyclohexyl)methoxy]cinnamate 27.6 ml of a 1.6 N butyllithium solution are added dropwise to a solution of 6.4 ml of trimethyl phosphonoacetate in 50 ml of dry tetrahydrofuran at 0° C. in the course of 10 minutes. Stirring is carried out for 1.5 hours at 0° C. and a solution of 10.3 g of crude 4-[(trans-4-heptylcyclohexyl)methoxy]benzaldehyde in 50 ml of dry tetrahydrofuran is then added dropwise in the course of 5 minutes at the same temperature. The mixture is then slowly warmed up to room temperature and is allowed to react for 15 hours. The reaction mixture is then partitioned between methylene chloride and 1 N hydrochloric acid and the organic phase is washed with saturated sodium bicarbonate solution and water, dried over magnesium sulfate and evaporated down. Chromatography over silica gel using ethyl acetate/hexane (1:9) and subsequent repeated crystallization from hexane/ethyl acetate give methyl 4-[(trans-4-heptylcyclohexyl)methoxy]cinnamate.

4-[(trans-4-heptylcyclohexyl)methoxy]cinnamic acid

A mixture of 8 g of methyl 4-[(trans-4-heptylcyclohexyl)methoxy]cinnamate and 50 ml of 10 percent methanolic potassium hydroxide solution is allowed to stand for 16 hours at room temperature. Thereafter, acidification is effected with aqueous 1 N sulfuric acid with continuous stirring and with cooling, extraction is effected with methylene chloride and the organic phase is washed several times with water, dried over magnesium sulfate and evaporated down. Crystallization from hexane/ethyl acetate gives 4-[(trans-4-heptylcyclohexyl)methoxy]cinnamic acid.

The following silane derivatives can be prepared in an analogous manner:

6-triethoxysilanylhexyl (E)-4-(4-methoxyphenyl)cinnamate;
6-triethoxysilanylhexyl (E)-4-(4-trifluoromethoxy-phenyl)cinnamate;
6-triethoxysilanylhexyl (E)-4-(4-decyloxyphenyl)-cinnamate;
6-triethoxysilanylhexyl (E)-4-[4-(3,3,4,4,5,5,6,6,6-nonafluorohexyloxy)phenyl]cinnamate;
6-triethoxysilanylhexyl (E)-4-(3,4-dimethoxyphenyl)cinnamate;
6-triethoxysilanylhexyl (E)-4-(3-methoxy-4-octyloxyphenyl)cinnamate;
6-triethoxysilanylhexyl (E)-4-(3-octyloxy-4-methoxyphenyl)cinnamate;
6-triethoxysilanylhexyl (E)-4-(4-ethylphenyl)cinnamate;
6-triethoxysilanylhexyl (E)-4-(4-hexylphenyl)cinnamate;
6-triethoxysilanylhexyl (E)-4-(trans-4-pentylcyclohexyl)cinnamate;
6-triethoxysilanylhexyl (E)-4-(cis-4-pentylcyclohexyl)cinnamate;
6-triethoxysilanylhexyl (E)-4-[(trans-4-heptylcyclohexyl)methoxy]cinnamate;
6-triethoxysilanylhexyl (E)-4-[(cis-4-heptylcyclohexyl)methoxy]cinnamate;
6-triethoxysilanylhexyl (E)-4-[4-(trans-4-pentylcyclohexyl)phenyl]cinnamate;
6-triethoxysilanylhexyl (E)-4-[4-(cis-4-pentylcyclohexyl)phenyl]cinnamate;
6-triethoxysilanylhexyl (E)-4-{4-[(trans-4-octylcyclohexyl)methoxy]phenyl}cinnamate;
6-triethoxysilanylhexyl (E)-4-{4-[(cis-4-heptylcyclohexyl)methoxy]phenyl}cinnamate;
6-triethoxysilanylhexyl (E)-4-{trans-4-[(trans-4-pentylcyclohexyl)cyclohexyl]methoxy}cinnamate;
6-triethoxysilanylhexyl (E)-4-{cis-4-[(trans-4-pentylcyclohexyl)cyclohexyl]methoxy}cinnamate;
6-triethoxysilanylhexyl (E)-4-{trans-4-[(cis-4-pentylcyclohexyl)cyclohexyl]methoxy}cinnamate;

EXAMPLE 4

6-(3-Triethoxysilanylpropylcarbamoyloxy)hexyl (E)-3-(6-heptyloxynaphth-2-yl)acrylate The compound is prepared analogously to Example 1 by esterification of (E)-3-(6-heptyloxynaphth-2-yl)acrylic acid with 6-chlorohexanol and subsequent reaction of the resulting 6-hydroxyhexyl (E)-3-(6-heptyloxynaphth-2-yl)acrylate with 3-triethoxysilanylpropyl isocyanate.

The (E)-3-(6-heptyloxynaphth-2-yl)acrylic acid used as a starting material is prepared by the following process:

6-Bromo-2-heptyloxynaphthalene

A mixture of 5 g of 6-bromo-2-naphthol, 50 ml of dimethyl sulfoxide, 3.9 ml of 6-bromoheptane, 7.1 g of potassium iodide and 7.1 g of milled potassium carbonate activated at 80° C. in high vacuum is heated to 65° C. for 16 hours. It is then cooled and is partitioned between ethyl acetate and water and the organic phase is washed several times with water, dried over magnesium sulfate, filtered and evaporated down. Chromatography of the residue over 200 g of silica gel using toluene and subsequent crystallization from toluene/hexane (8:1) give 6-bromo-2-heptyloxynaphthalene.

Methyl (E)-3-(6-heptyloxynaphth-2-yl)acrylate

A mixture of 5.2 g of 6-bromo-2-heptyloxynaphthalene, 25 ml of triethylamine, 4.3 ml of methyl acrylate, 0.072 g of palladium acetate and 0.392 g of tri-o-tolylphosphine is refluxed for 16 hours. The reaction mixture is then cooled and is partitioned between ethyl acetate and water and the organic phase is washed with water, dried over magnesium sulfate, filtered and evaporated down. The residue is chromatographed over 250 g of silica gel using toluene/ethyl acetate (3:1) and then crystallized from toluene. This gives methyl (E)-3-(heptyloxynaphth-2-yl)acrylate.

(E)-3-(6-heptyloxynaphth-2-yl)acrylic acid

A mixture of 0.8 g of methyl (E)-3-(heptyloxynaphth-2-yl)acrylate and 10 ml of 10 percent methanolic potassium hydroxide solution is allowed to stand for 16 hours at room temperature. Thereafter, acidification is effected with aqueous 1 N sulfuric acid with continuous stirring and with cooling, extraction is effected with methylene chloride and the organic phase is washed several times with water, dried over magnesium sulfate and evaporated down. Crystallization from hexane/ethyl acetate gives (E)-3-(6-heptyloxynaphth-2-yl)acrylic acid.

The following silanes can be synthesized in an analogous manner:

6-(3-triethoxysilanylpropylcarbamoyloxy)hexyl (E)-3-(6-ethoxynaphth-2-yl)acrylate;
6-(3-triethoxysilanylpropylcarbamoyloxy)hexyl (E)-3-(6-propoxynaphth-2-yl)acrylate;
6-(3-triethoxysilanylpropylcarbamoyloxy)hexyl (E)-3-(6-butoxynaphth-2-yl)acrylate;
6-(3-triethoxysilanylpropylcarbamoyloxy)hexyl (E)-3-(6-pentyloxynaphth-2-yl)acrylate;
6-(3-triethoxysilanylpropylcarbamoyloxy)hexyl (E)-3-(6-hexyloxynaphth-2-yl)acrylate;
6-(3-triethoxysilanylpropylcarbamoyloxy)hexyl (E)-3-(6octyloxynaphth-2-yl)acrylate;
6-(3-triethoxysilanylpropylcarbamoyloxy)hexyl (E)-3-(6-dodecyloxynaphth-2-yl)acrylate;
4-(3-triethoxysilanylpropylcarbamoyloxy)butyl (E)-3-(6-heptyloxynaphth-2-yl)acrylate;
5-(3-triethoxysilanylpropylcarbamoyloxy)pentyl (E)-3-(6-heptyloxynaphth-2-yl)acrylate;
8-(3-triethoxysilanylpropylcarbamoyloxy)octyl (E)-3-(6-heptyloxynaphth-2-yl)acrylate;
6-(2-triethoxysilanylethylcarbamoyloxy)hexyl (E)-3-(6-heptyloxynaphth-2-yl)acrylate;
6-(2-triethoxysilanylethylcarbamoyloxy)hexyl (E)-3-{6-[(trans-4-propylcyclohexyl)methoxy]naphth-2-yl}acrylate;
6-(2-triethoxysilanylethylcarbamoyloxy)hexyl (E)-3-{6-[(cis-4-propylcyclohexyl)methoxy]naphth-2-yl}acrylate;
6-(2-triethoxysilanylethylcarbamoyloxy)hexyl (E)-3-{6-[(trans-4-decylcyclohexyl)methoxy]naphth-2-yl}acrylate;
6-(2-triethoxysilanylethylcarbamoyloxy)hexyl (E)-3-{6-[(cis-4-decylcyclohexyl)methoxy]naphth-2-yl}acrylate.

EXAMPLE 5

6-Trichlorosilanylhexyl (E)-3,4-dimethoxycinnamate 5 ml of trichlorosilane are added to a solution of 0.1 g of $H_2PtCl_6$ in 20 ml of dry tetrahydrofuran while stirring. A solution of 14.8 g of hex-5-enyl (E)-3,4- dimethoxycinnamate, dissolved in 20 ml of dry tetrahydrofuran, is carefully added dropwise to this. Thereafter, stirring is carried out for 5 hours at room temperature and then for 16 hours at 50° C. The reaction mixture is concentrated in a vacuum produced by a water-jet pump and is completely freed from the remaining solvent and trichlorosilane by means of an oil pump with a cold trap under reduced pressure. This gives crude 6-trichlorosilanylhexyl (E)-3,4-dimethoxycinnamate, which is dissolved in dry tetrahydrofuran for storage.

The preparation of the hex-5-enyl (E)-3,4-dimethoxycinnamate required as the starting material is described in Example 2.

The following silane derivatives can be prepared in an analogous manner:

6-trichlorosilanylhexyl (E)-2-methoxycinnamate;
8-trichlorosilanyloctyl (E)-3-methoxycinnamate;
6-trichlorosilanylhexyl (E)-3-hexyloxycinnamate;
6-trichlorosilanylhexyl (E)-4-methoxycinnamate;
6-trichlorosilanylhexyl (E)-4-ethoxycinnamate;
6-trichlorosilanylhexyl (E)-4-propoxycinnamate;
8-trichlorosilanyloctyl (E)-4-butoxycinnamate;
6-trichlorosilanylhexyl (E)-4-pentyloxycinnamate;
6-trichlorosilanylhexyl (E)-4-hexyloxycinnamate;
8-trichlorosilanyloctyl (E)-4-dodecyloxycinnamate;
8-trichlorosilanyloctyl (E)-3-fluorocinnamate;
8-trichlorosilanyloctyl (E)-4-fluorocinnamate;
8-trichlorosilanyloctyl (E)-3-chlorocinnamate;
8-trichlorosilanyloctyl (E)-4-chlorocinnamate;
6-trichlorosilanylhexyl (E)-4-trifluoromethoxycinnamate;
6-trichlorosilanylhexyl (E)-4-acetamidocinnamate;
8-trichlorosilanyloctyl (E)-4-acetamidocinnamate;
6-trichlorosilanylhexyl (E)-4-pentanoylaminocinnamate;
6-trichlorosilanylhexyl (E)-4-decanoylaminocinnamate;
5-trichlorosilanylpentyl (E)-3,4-dimethoxycinnamate;
7-trichlorosilanylheptyl (E)-3,4-dimethoxycinnamate;
8-trichlorosilanyloctyl (E)-3,4-dimethoxycinnamate;
9-trichlorosilanylnonyl (E)-3,4-dimethoxycinnamate;
10-trichlorosilanyldecyl (E)-3,4-dimethoxycinnamate;
11-trichlorosilanylundecyl (E)-3,4-dimethoxycinnamate;
12-trichlorosilanyldodecyl (E)-3,4-dimethoxycinnamate;
6-trichlorosilanylhexyl (E)-3,5-dimethoxycinnamate;
6-trichlorosilanylhexyl (E)-2,5-dimethoxycinnamate;
6-trichlorosilanylhexyl (E)-3-methoxy-4-propoxycinnamate;
6-trichlorosilanylhexyl (E)-3-methoxy-4-octyloxycinnamate;
6-trichlorosilanylhexyl (E)-3-decyloxy-4-methoxycinnamate;
7-trichlorosilanylheptyl (E)-3-fluoro-4-methoxycinnamate;
8-trichlorosilanyloctyl (E)-3-chloro-4-methoxycinnamate;
6-trichlorosilanylhexyl (E)-3-propyl-4-methoxycinnamate;
8-trichlorosilanyloctyl (E)-3,4,5-trimethoxycinnamate;
9-trichlorosilanylnonyl (E)-3,4-difluorocinnamate;
10-trichlorosilanyldecyl (E)-2,3-difluorocinnamate;
6-trichlorosilanylhexyl (E)-3,4,5-trifluorocinnamate;
8-trichlorosilanyloctyl (E)-3-fluoro-4-chlorocinnamate;
6-trichlorosilanylhexyl (E)-3-ethoxy-4-acetamidocinnamate;
6-trichlorosilanylhexyl (E)-4-(4-methoxybenzoyloxy)cinnamate;
6-trichlorosilanylhexyl (E)-3-methoxy-4-(4-methoxybenzoyloxy)cinnamate;
6-trichlorosilanylhexyl (E)-4-(3,4-dimethoxybenzyloxy)cinnamate;
6-trichlorosilanylhexyl (E)-3-methoxy-4-(3,4-dimethoxybenzyloxy)cinnamate;
8-trichlorosilanyloctyl (E)-3-ethoxy-4-(3,4-dimethoxybenzyloxy)cinnamate;
8-trichlorosilanyloctyl (E)-4-(4-methoxyphenyl)cinnamate;
8-trichlorosilanyloctyl (E)-4-(4-trifluoromethoxy-phenyl)cinnamate;
6-trichlorosilanylhexyl (E)-4-(4-decyloxyphenyl)cinnamate;
6-trichlorosilanylhexyl (E)-4-[4-(6,6,6-trifluorohexyloxy)phenyl]cinnamate;
8-trichlorosilanyloctyl (E)-4-(3,4-dimethoxyphenyl)cinnamate;
6-trichlorosilanylhexyl (E)-4-(3-methoxy-4-hexyloxyphenyl)cinnamate;
6-trichlorosilanylhexyl (E)-4-(3-hexyloxy-4-methoxyphenyl)cinnamate;
6-trichlorosilanylhexyl (E)-4-(4-propylphenyl)cinnamate;
6-trichlorosilanylhexyl (E)-4-(4-decylphenyl)cinnamate;
6-trichlorosilanylhexyl (E)-4-(trans-4-hexylcyclohexyl)cinnamate;
6-trichlorosilanylhexyl (E)-4-(cis-4-heptylcyclohexyl)cinnamate;
6-trichlorosilanylhexyl (E)-4-[(trans-4-hexylcyclohexyl)methoxy]cinnamate;
6-trichlorosilanylhexyl (E)-4-[(cis-4-hexylcyclohexyl)methoxy]cinnamate;
6-trichlorosilanylhexyl (E)-4-[4-(trans-4-pentylcyclohexyl)phenyl]cinnamate;
6-trichlorosilanylhexyl (E)-4-[4-(cis-4-pentylcyclohexyl)phenyl]cinnamate;
6-trichlorosilanylhexyl (E)-4-{4-[(trans-4-hexylcyclohexyl)methoxy]phenyl}cinnamate;
6-trichlorosilanylhexyl (E)-4-{4-[(cis-4-heptylcyclohexyl)methoxy]phenyl}cinnamate;
6-trichlorosilanylhexyl (E)-4-{trans-4-[(trans-4-pentylcyclohexyl)cyclohexyl]methoxy}cinnamate;
6-trichlorosilanylhexyl (E)-4-{cis-4-[(trans-4-hexylcyclohexyl)cyclohexyl]methoxy}cinnamate;
6-trichlorosilanylhexyl (E)-4-{trans-4-[(cis-4-heptylcyclohexyl)cyclohexyl]methoxy}cinnamate.

EXAMPLE 6

Production of a Photocrosslinkable Layer 0.02 g of 6-(3-triethoxysilanylpropylcarbamoyloxy)hexyl (E)-3,4-dimethoxycinnamate was dissolved in 2 ml of propanol. This solution was applied to a cleaned glass sheet (19×26 mm) by spin-coating at 1000 rpm and then heated at a temperature of 130° C. for 30 minutes.

The glass sheet treated in this manner was then cleaned with ethanol in an ultrasonic bath for 15 minutes.

EXAMPLE 7

Production of an Orientation Layer for Liquid Crystals

The coated glass sheet described in Example 6 was exposed to the linearly polarized UV light of a high-pressure mercury lamp for one minute. The liquid crystal layer was then applied to the coated sheet by spin-coating. A uniaxially birefringent layer of oriented liquid crystal molecules could then be observed thereon under the polarization microscope. With the aid of a tilt compensator, it was found that the orientation direction corresponds to the polarization direction of the UV light set during exposure of the silane layer.

EXAMPLE 8

Production of an Orientation Layer Having a Defined Tilt Angle

Two glass sheets coated according to Example 6 with 6-(3-triethoxysilanylpropylcarbamoyloxy)hexyl (E)-3,4- dimethoxycinnamate were exposed to linearly polarized UV light for 3 minutes, the direction of incidence of the light being inclined 70° relative to the sheet normal. The polarization direction of the light was in the plane defined by the direction of incidence of the light and the sheet normal. The two sheets were then assembled, with the coated side facing inward, to give a liquid crystal cell having a sheet spacing of 20 mm, so that the directions defined by polarization and light incidence during exposure of the sheets were parallel to one another. The cell was then filled with the liquid crystal mixture 3010 from ROLIC AG at a temperature of 100° C., the liquid crystal mixture being in the isotropic phase during the filling procedure. The cell was then gradually cooled to room temperature at a rate of 1° C./min. A uniformly oriented liquid crystal layer was then detected between cross polarizers. The tilt angle of this parallel cell, measured with the aid of the crystal rotation method, was 0.2°.

What is claimed is:

1. A silane of the general formula I:

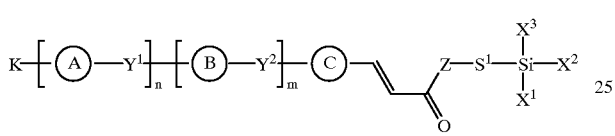

in which
- $X^1$, $X^2$ and $X^3$ denote alkyl, alkoxy or halogen, but at least one of these radicals is either alkoxy or halogen;
- $S^1$ denotes a spacer unit or denotes a chain of the formula —$(CH_2)_r$—L—$(CH_2)_s$—, in which L denotes a single bond or linking functional group and r and s each represent an integer from 1 to 20, with the proviso that r+s is $\leq 25$;
- Ring A denotes unsubstituted or fluorine-, chlorine-, cyano-, alkyl- or alkoxy-substituted phenylene, pyrid-2,5-diyl, pyrimidin-2,5-diyl, 1,3-dioxane-2,5-diyl, cyclohexane-1,4-diyl, piperidin-1,4-diyl or piperazin-1,4-diyl, it being possible for the alkyl and/or the alkoxy substituent to be mono- or polysubstituted by fluorine;
- Ring B denotes unsubstituted or fluorine-, chlorine-, cyano-, alkyl- or alkoxy-substituted phenylene, pyrid-2,5-diyl, pyrimidin-2,5-diyl, 1,4- or 2,6-naphthylene, 1,3-dioxane-2,5-diyl or cyclohexane-1,4-diyl, it being possible for the alkyl and/or the alkoxy substituent to be mono- or polysubstituted by fluorine;
- K is hydrogen, fluorine, chlorine, cyano, nitro or a straight-chain or branched alkyl, alkoxy, alkyl-COO, alkyl-CO—$NR^2$ or alkyl-OCO group having 1 to 20 carbon atoms which is optionally substituted by fluorine, chlorine, cyano or nitro and in which optionally one $CH_2$ group or a plurality of non-neighboring $CH_2$ groups may be replaced by O, CH=CH or C≡C and in which $R^2$ denotes hydrogen or lower alkyl;
- $Y^1$ and $Y^2$ independently of one another, denote a single covalent bond, —$(CH_2)_t$—, —O—, —CO—, —CO—O—, —O—OC—, —$NR^3$—, —CO—$NR^3$—, —$R^3$N—CO—, —$(CH_2)_u$—O—, —O—$(CH_2)_u$—, —$(CH_2)_u$—$NR^3$— or $NR^3$—$(CH_2)_u$—, in which
- $R^3$ denotes hydrogen or lower alkyl;
- t denotes an integer from 1 to 4;
- u denotes an integer from 1 to 3;
- m and n, independently of one another, denote 0 or 1;

- Ring C denotes unsubstituted or fluorine-, chlorine-, cyano-, alkyl- or alkoxy-substituted phenylene, pyrimidin-2,5- or 3,5-diyl, pyrid-2,5- or -2,4-diyl or -2,6-diyl, 2,5-thiophenylene, 2,5-furanylene, 1,4- or 2,6-naphthylene, it being possible for the alkyl and/or the alkoxy substituent to be mono- or polysubstituted by fluorine;
- Z denotes —O— or —$NR^4$— and $R^4$ denotes hydrogen or lower alkyl, with the proviso that K is not hydrogen when simultaneously m is 0, n is 0, and Ring C is unsubstituted phenylene.

2. The silane of the general formula I as claimed in claim 1, wherein $X^1$, $X^2$, $X^3$, $S^1$, K, m and n have the meaning stated in claim 1 and
- Ring A denotes unsubstituted or fluorine-, chlorine-, cyano-, alkyl- or alkoxy-substituted phenylene, pyrid-2,5-diyl, pyrimidin-2,5-diyl or cyclohexane-1,4-diyl, it being possible for the alkyl and/or the alkoxy substituent to be mono- or polysubstituted by fluorine;
- Ring B denotes unsubstituted or fluorine-, chlorine-, cyano-, alkyl- or alkoxy-substituted phenylene, pyrid-2,5-diyl, pyrimidin-2,5-diyl, 1,4- or 2,6-naphthylene or cyclohexane-1,4-diyl, it being possible for the alkyl and/or the alkoxy substituent to be mono- or polysubstituted by fluorine;
- $Y^1$ and $Y^2$, independently of one another, denote a single covalent bond, —$CH_2CH_2$—, —O—, —$CH_2$—O—, —O—$CH_2$—, —CO—O— or —O—OC—;
- Ring C denotes unsubstituted or fluorine-, chlorine-, cyano-, alkyl- or alkoxy-substituted 1,3- or 1,4-phenylene, pyrimidin-2,5-diyl, pyrid-2,5-diyl, 2,5-furanylene or 1,4- or 2,6-naphthylene, it being possible for the alkyl and/or the alkoxy substituent to be mono- or polysubstituted by fluorine;
- Z denotes —O—.

3. The silane of the general formula I as claimed in claim 1, wherein $X^1$, $X^2$, $X^3$, $S^1$, K and m have the meaning stated in claim 1 and
- n denotes 0;
- Ring B denotes unsubstituted or fluorine-, chlorine-, cyano-, alkyl- or alkoxy-substituted phenylene, pyrid-2,5-diyl, pyrimidin-2,5-diyl or cyclohexane-1,4-diyl, it being possible for the alkyl and/or the alkoxy substituent to be mono- or polysubstituted by fluorine;
- $Y^2$ denotes a single covalent bond, —CO—O— or —$CH_2$—O—;
- Ring C denotes unsubstituted or fluorine-, chlorine-, cyano-, alkyl or alkoxy- substituted 1,3- or 1,4-phenylene, or 1,4- or 2,6-naphthylene, it being possible for the alkyl and/or the alkoxy substituent to be mono- or polysubstituted by fluorine;
- Z denotes —O—.

4. The silane as claimed in claim 3, 6-(3-triethoxysilanylpropylcarbamoyloxy)hexyl (E)-3,4-dimethoxycinnamate;
6-triethoxysilanylhexyl (E)-3,4-dimethoxycinnamate;
6-trichlorosilanylhexyl (E)-3,4-dimethoxycinnamate;
6-triethoxysilanylhexyl (E)-4-[(trans-4-heptylcyclohexyl)methyl]cinnamate;
6-(3-triethoxysilanylpropylcarbamoyloxy)hexyl (E)-3-(6-heptyloxynaphth-2-yl)acrylate.

5. A crosslinkable mixture comprising at least two components at least one of which is a photocrosslinkable silane derivative of the formula I:

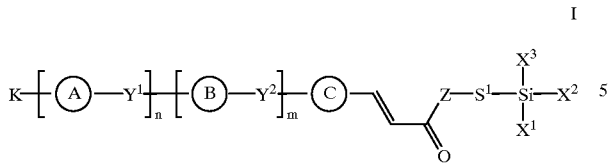

I

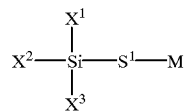

II in which:

X$^1$, X$^2$ and X$^3$ denote alkyl, alkoxy or halogen, but at least one of these radicals is either alkoxy or halogen;

S$^1$ denotes a spacer unit or denotes a chain of the formula —(CH$_2$)$_r$—L—(CH$_2$)$_s$—, in which L denotes a single bond or linking functional group and r and s each represent an integer from 1 to 20, with the proviso that r+s is ≦25;

Ring A denotes unsubstituted or fluorine-, chlorine-, cyano-, alkyl- or alkoxy-substituted phenylene, pyrid-2,5-diyl, pyrimidin-2,5-diyl, 1,3-dioxane-2,5-diyl, cyclohexane-1,4-diyl, piperidin-1,4-diyl or piperazin-1,4-diyl, it being possible for the alkyl and/or the alkoxy substituent to be mono- or polysubstituted by fluorine;

Ring B denotes unsubstituted or fluorine-, chlorine-, cyano-, alkyl- or alkoxy-substituted phenylene, pyrid-2,5-diyl, pyrimidin-2,5-diyl, 1,4- or 2,6-naphthylene, 1,3-dioxane-2,5-diyl or cyclohexane-1,4-diyl, it being possible for the alkyl and/or the alkoxy substituent to be mono- or polysubstituted by fluorine;

K is hydrogen, fluorine, chlorine, cyano, nitro or a straight-chain or branched alkyl, alkoxy, alkyl —COO, alkyl-CO—NR$^2$ or alkyl-OCO group having 1 to 20 carbon atoms which is optionally substituted by fluorine, chlorine, cyano or nitro and in which optionally one CH$_2$ group or a plurality of non-neighboring CH$_2$ groups may be replaced by O, CH═CH or C≡C and in which R$^2$ denotes hydrogen or lower alkyl;

Y$^1$ and Y$^2$ independently of one another, denote a single covalent bond, —(CH$_2$)$_t$—, —O—, —CO—, —CO—O—, —O—OC—, —NR$^3$—, —CO—NR$^3$—, —R$^3$N—CO—, —(CH$_2$)$_u$—O—, —O—(CH$_2$)$_u$—, —(CH$_2$)$_u$—NR$^3$— or NR$^3$—(CH$_2$)$_u$—, in which R$^3$ denotes hydrogen or lower alkyl;

t denotes an integer from 1 to 4;

u denotes an integer from 1 to 3;

m and n, independently of one another, denote 0 or 1;

Ring C denotes unsubstituted or fluorine-, chlorine-, cyano-, alkyl- or alkoxy-substituted phenylene, pyrimidin-2,5- or 3,5-diyl, pyrid-2,5- or -2,4-diyl or -2,6-diyl, 2,5-thiophenylene, 2,5-furanylene, 1,4- or 2,6-naphthylene, it being possible for the alkyl and/or the alkoxy substituent to be mono- or polysubstituted by fluorine;

Z denotes —O— or —NR$^4$— and R$^4$ denotes hydrogen or lower alkyl with the proviso that K is not hydrogen when simultaneously m is 0, n is 0, and Ring C is unsubstituted phenylene.

6. The crosslinkable mixture as claimed in claim 5, which, in addition to one or more photocrosslinkable silane derivatives of the formula I defined in claim 1, contains one or more uncrosslinkable silane derivatives of the general formula II in which X$^1$, X$^2$, X$^3$ and S$^1$ have the meaning stated in claim 1 and M denotes lower alkyl, lower alkyl mono- or polysubstituted by fluorine, lower alkoxy, lower alkoxy mono- or polysubstituted by fluorine, or a mesogenic radical of the general formula III

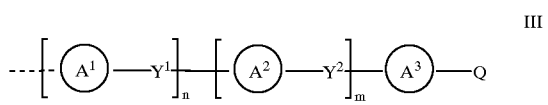

III in which

Y$^1$, Y$^2$, m and n have the meaning stated in claim 1 and A$^1$, A$^2$ and A$^3$ denote unsubstituted or fluorine-, chlorine-, cyano-, alkyl- or alkoxy-substituted phenylene, pyrid-2,5-diyl, pyrimidin-2,5-diyl, 2,6-naphthylene, 1,3-dioxane-2,5-diyl or cyclohexane-1, 4-diyl, it being possible for the alkyl and/or the alkoxy substituent to be mono- or polysubstituted by fluorine and not more than one of the rings differing from phenylene or cyclohexylene;

Q denotes lower alkyl or alkoxy in which one or more hydrogen atoms may be replaced by fluorine, or denotes fluorine, chlorine, cyano or nitro.

7. The crosslinkable mixture as claimed in claim 6, wherein n denotes 0;

m denotes 0 or 1;

A$^2$ and A$^3$ denote phenylene or cyclohexylene;

Y$^1$ and Y$^2$ denote a single covalent bond, —CH$_2$CH$_2$—, —O—, —CH$_2$—O—, —O—CH$_2$—, —CO—O— or —O—OC—;

Q denotes optionally fluorine-substituted lower alkyl or alkoxy, fluorine, chlorine or cyano.

8. The crosslinkable mixture as claimed in claim 7, wherein m denotes 0;

A$^3$ denotes phenylene or cyclohexylene;

Q denotes optionally fluorine-substituted lower alkyl or alkoxy.

9. A method of producing an orientation layer for liquid crystals and of hybrid layer elements, comprising the step of applying to a carrier a photocrosslinkable silane derivative of the formula I:

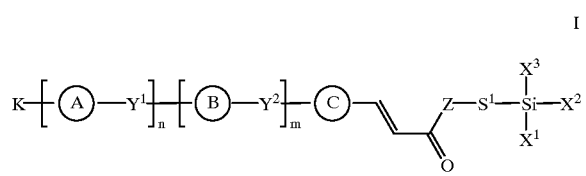

I in which:

X$^1$, X$^2$ and X$^3$ denote alkyl, alkoxy or halogen, but at least one of these radicals in either alkoxy or halogen:

$S^1$ denotes a spacer unit or denotes a chain of the formula —(CH$_2$)$_r$—L—(CH$_2$)$_s$—, in which L denotes a single bond or linking functional groups, such as O, COO, OOC, NR$^1$, NR$^1$—CO—, CO—NR$^1$, NR$^1$—COO, OCO—NR$^1$, NR$^1$—CO—NR$^1$, —CH=CH— or —C≡C—, R$^1$ denotes hydrogen or lower alkyl and r and s each represent an integer from 1 to 20, with the proviso that r+s is ≦25;

Ring A denotes unsubstituted or fluorine-, chlorine-, cyano-, alkyl- or alkoxy-substituted phenylene, pyrid-2,5-diyl, pyrimidin-2,5-diyl, 1,3-dioxane-2,5-diyl, cyclohexane-1,4-diyl, piperidin-1,4-diyl or piperazin-1,4-diyl, it being possible for the alkyl and/or the alkoxy substituent to be mono- or polysubstituted by fluorine;

Ring B denotes unsubstituted or fluorine-, chlorine-, cyano-, alkyl- or alkoxy-substituted phenylene, pyrid-2,5-diyl, pyrimidin-2,5-diyl, 1,4- or 2,6-naphthylene, 1,3-dioxane-2,5-diyl or cyclohexane-1,4-diyl, it being possible for the alkyl and/or the alkoxy substituent to be mono- or polysubstituted by fluorine;

K is hydrogen, fluorine, chlorine, cyano, nitro or a straight-chain or branched alkyl, alkoxy, alkyl-COO, alkyl-CO—NR$^2$ or alkyl-OCO group having 1 to 20 carbon atoms which is optionally substituted by fluorine, chlorine, cyano or nitro and in which optionally one CH$_2$ group or a plurality of non-neighboring CH$_2$ groups may be replaced by O, CH=CH or C≡C and in which R$^2$ denotes hydrogen or lower alkyl;

Y$^1$ and Y$^2$, independently of one another, denote a single covalent bond, —(CH$_2$)$_t$—, —O—, —CO—, —CO—O—, —O—OC—, —NR$^3$—, —CO—NR$^3$—, —R$^3$N—CO—, —(CH$_2$)$_u$—O—, —O—(CH$_2$)$_u$—, —(CH$_2$)$_u$—NR$^3$— or NR$^3$—(CH$_2$)$^d$—, in which R$^3$ denotes hydrogen or lower alkyl;

t denotes an integer from 1 to 4;

u denotes an integer from 1 to 3;

m and n, independently of one another, denote 0 or 1;

Ring C denotes unsubstituted or fluorine-, chlorine-, cyano-, alkyl- or alkoxy-substituted phenylene, pyrimidin-2,5- or 3,5-diyl, pyrid-2,5- or -2,4-diyl or -2,6-diyl, 2,5-thiophenylene, 2,5-furanylene, 1,4- or 2,6-naphthylene, it being possible for the alkyl and/or the alkoxy substituent to be mono- or polysubstituted by fluorine;

Z denotes —O— or —NR$^4$— and R$^4$ denotes hydrogen or lower alkyl.

10. A method of producing of orientation layers for liquid crystals and of hybrid layer elements, comprising the step of applying to a carrier a crosslinkable mixture comprising at least two components at least one of which is a photocrosslinkable silane derivative of the formula I:

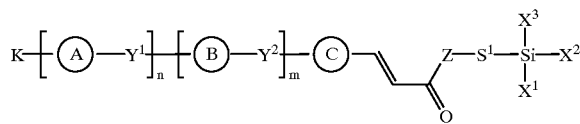

I in which:

X$^1$, X$^2$ and X$^3$ denote alkyl, alkoxy or halogen, but at least one of these radicals in either alkoxy or halogen:

S$^1$ denotes a spacer unit or denotes a chain of the formula —(CH$_2$)$_r$—L—(CH$_2$)$_s$—, in which L denotes a single bond or linking functional groups, such as O, COO, OOC, NR$^1$, NR$^1$—CO—, CO—NR$^1$, NR$^1$—COO, OCO—NR$^1$, NR$^1$—CO—NR$^1$, —CH=CH— or —C≡C—, R$^1$ denotes hydrogen or lower alkyl and r and s each represent an integer from 1 to 20, with the proviso that r+s is ≦25;

Ring A denotes unsubstituted or fluorine-, chlorine-, cyano-, alkyl- or alkoxy-substituted phenylene, pyrid-2,5-diyl, pyrimidin-2,5-diyl, 1,3-dioxane-2,5-diyl, cyclohexane-1,4-diyl, piperidin-1,4-diyl or piperazin-1,4-diyl, it being possible for the alkyl and/or the alkoxy substituent to be mono- or polysubstituted by fluorine;

Ring B denotes unsubstituted or fluorine-, chlorine-, cyano-, alkyl- or alkoxy-substituted phenylene, pyrid-2,5-diyl, pyrimidin-2,5-diyl, 1,4- or 2,6-naphthylene, 1,3-dioxane-2,5-diyl or cyclohexane-1,4-diyl, it being possible for the alkyl and/or the alkoxy substituent to be mono- or polysubstituted by fluorine;

K is hydrogen, fluorine, chlorine, cyano, nitro or a straight-chain or branched alkyl, alkoxy, alkyl-COO, alkyl-CO—NR$^2$ or alkyl-OCO group having 1 to 20 carbon atoms which is optionally substituted by fluorine, chlorine, cyano or nitro and in which optionally one CH$_2$ group or a plurality of non-neighboring CH$_2$ groups may be replaced by O, CH=CH or C≡C and in which R$^2$ denotes hydrogen or lower alkyl;

Y$^1$ and Y$^2$, independently of one another, denote a single covalent bond, —(CH$_2$)$_t$—, —O—, —CO—, —CO—O—, —O—OC—, —NR$^3$—, —CO—NR$^3$—, —R$^3$N—CO—, —(CH$_2$)$_u$—O—, —O—(CH$_2$)$_u$—, —(CH$_2$)$_u$—NR$^3$— or NR$^3$—(CH$_2$)$_u$—, in which R$^3$ denotes hydrogen or lower alkyl;

t denotes an integer from 1 to 4;

u denotes an integer from 1 to 3;

m and n, independently of one another, denote 0 or 1;

Ring C denotes unsubstituted or fluorine-, chlorine-, cyano-, alkyl- or alkoxy-substituted phenylene, pyrimidin-2,5- or 3,5-diyl, pyrid-2,5- or -2,4-diyl or -2,6-diyl, 2,5-thiophenylene, 2,5-furanylene, 1,4- or 2,6-naphthylene, it being possible for the alkyl and/or the alkoxy substituent to be mono- or polysubstituted by fluorine;

Z denotes —O— or —NR$^4$— and R$^4$ denotes hydrogen or lower alkyl.

11. An orientation layer for liquid crystals, comprising a photocrosslinkable silane derivative of formula I:

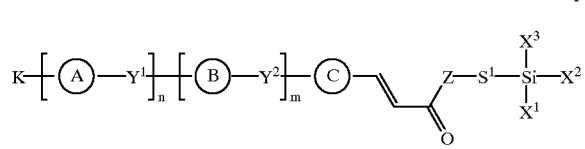

I in which:

X$^1$, X$^2$ and X$^3$ denote alkyl, alkoxy or halogen, but at least one of these radicals in either alkoxy or halogen:

S$^1$ denotes a spacer unit or denotes a chain of the formula —(CH$_2$)$_r$—L—(CH$_2$)$_s$—, in which L denotes a single bond or linking functional groups, such as O, COO, OOC, NR$^1$, NR$^1$—CO—, CO—NR$^1$, NR$^1$—COO, OCO—NR$^1$, NR$^1$—CO—NR$^1$, —CH=CH— or —C≡C—, R$^1$ denotes hydrogen or lower alkyl and r and s each represent an integer from 1 to 20, with the proviso that r+s is ≦25;

Ring A denotes unsubstituted or fluorine-, chlorine-, cyano-, alkyl- or alkoxy-substituted phenylene, pyrid-2,5-diyl, pyrimidin-2,5-diyl, 1,3-dioxane-2,5-diyl, cyclohexane-1,4-diyl, piperidin-1,4-diyl or piperazin-1,4-diyl, it being possible for the alkyl and/or the alkoxy substituent to be mono- or polysubstituted by fluorine;

Ring B denotes unsubstituted or fluorine-, chlorine-, cyano-, alkyl- or alkoxy-substituted phenylene, pyrid-2,5-diyl, pyrimidin-2,5-diyl, 1,4- or 2,6-naphthylene 1,3-dioxane-2,5-diyl or cyclohexane-1,4-diyl, it being possible for the alkyl and/or the alkoxy substituent to be mono- or polysubstituted by fluorine;

K is hydrogen, fluorine, chlorine, cyano, nitro or a straight-chain or branched alkyl, alkoxy, alkyl-COO, alkyl-CO—$NR^2$ or alkyl-OCO group having 1 to 20 carbon atoms which is optionally substituted by fluorine, chlorine, cyano or nitro and in which optionally one $CH_2$ group or a plurality of non-neighboring $CH_2$ groups may be replaced by O, CH=CH or C≡C and in which $R^2$ denotes, hydrogen or lower alkyl;

$Y^1$ and $Y^2$, independently of one another, denote a single covalent bond, —$(CH_2)_t$—, —O—, —CO—, —CO—O—, —O—OC—, —$NR^3$—, —CO—$NR^3$—, —$R^3N$—CO—, —$(CH_2)_u$—O—, —O—$(CH_2)_u$—, —$(CH_2)_u$—$NR^3$— or $NR^3$—$(CH_2)_u$—, in which $R^3$ denotes hydrogen or lower alkyl;

t denotes an integer from 1 to 4;

u denotes an integer from 1 to 3;

m and n, independently of one another, denote 0 or 1;

Ring C denotes unsubstituted or fluorine-, chlorine-, cyano-, alkyl- or alkoxy-substituted phenylene, pyrimidin-2,5- or 3,5-diyl, pyrid-2,5- or -2,4-diyl or -2,6-diyl, 2,5-thiophenylene, 2,5-furanylene, 1,4- or 2,6-naphthylene, it being possible for the alkyl and/or the alkoxy substituent to be mono- or polysubstituted by fluorine;

Z denotes —O— or —$NR^4$— and $R^4$ denotes hydrogen or lower alkyl.

12. A hybrid layer element, comprising a photocrosslinkable silane derivative of the formula I:

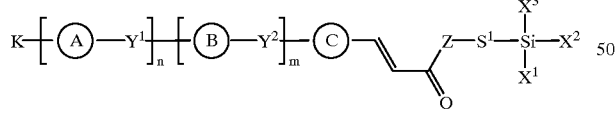

in which:

$X^1$, $X^2$ and $X^3$ denote alkyl, alkoxy or halogen, but at least one of these radicals in either alkoxy or halogen:

$S^1$ denotes a spacer unit or denotes a chain of the formula —$(CH_2)_r$—L—$(CH_2)_s$—, in which L denotes a single bond or linking functional groups, such as O, COO, OOC, $NR^1$, $NR^1$—CO—, CO—$NR^1$, $NR^1$—COO, OCO—$NR^1$, $NR^1$—CO—$NR^1$, —CH=CH— or —C≡C—, $R^1$ denotes hydrogen or lower alkyl and r and s each represent an integer from 1 to 20, with the proviso that r+s is ≦25;

Ring A denotes unsubstituted or fluorine-, chlorine-, cyano-, alkyl- or -alkoxy-substituted phenylene, pyrid-2,5-diyl, pyrimidin-2,5-diyl, 1,3-dioxane-2,5-diyl, cyclohexane-1,4-diyl, piperidin-1,4-diyl or piperazin-1,4-diyl, it being possible for the alkyl and/or the alkoxy substituent to be mono- or polysubstituted by fluorine;

Ring B denotes unsubstituted or fluorine-, chlorine-, cyano-, alkyl- or alkoxy-substituted phenylene, pyrid-2,5-diyl, pyrimidin-2,5-diyl, 1,4- or 2,6-naphthylene, 1,3-dioxane-2,5-diyl or cyclohexane-1,4-diyl, it being possible for the alkyl and/or the alkoxy substituent to be mono- or polysubstituted by fluorine;

K is hydrogen, fluorine, chlorine, cyano, nitro or a straight-chain or branched alkyl, alkoxy, alkyl-COO, alkyl-CO—$NR^2$ or alkyl-OCO group having 1 to 20 carbon atoms which is optionally substituted by fluorine, chlorine, cyano or nitro and in which optionally one $CH_2$ group or a plurality of non-neighboring $CH_2$ groups may be replaced by O, CH=CH or C≡C and in which $R^2$ denotes hydrogen or lower alkyl;

$Y^1$ and $Y^2$, independently of one another, denote a single covalent bond, —$(CH_2)_t$—, —O—, —CO—, —CO—O—, —O—OC—, —$NR^3$—, —CO—$NR^3$—, —$R^3N$—CO—, —$(CH_2)_u$—O—, —O—$(CH_2)_u$—, —$(CH_2)_u$—$NR^3$— or $NR^3$—$(CH_2)_u$—, in which $R^3$ denotes hydrogen or lower alkyl;

t denotes an integer from 1 to 4;

u denotes an integer from 1 to 3;

m and n, independently of one another, denote 0 or 1;

Ring C denotes unsubstituted or fluorine-, chlorine-, cyano-, alkyl- or alkoxy-substituted phenylene, pyrimidin-2,5- or 3,5-diyl, pyrid-2,5- or -2,4-diyl or -2,6-diyl, 2,5-thiophenylene, 2,5-furanylene, 1,4- or 2,6-naphthylene, it being possible for the alkyl and/or the alkoxy substituent to be mono- or polysubstituted by fluorine;

Z denotes —O— or —$NR^4$— and $R^4$ denotes hydrogen or lower alkyl.

13. An orientation layer for liquid crystals, comprising a crosslinkable mixture having at least two components at least one of which is a photocrosslinkable silane derivative of the formula I:

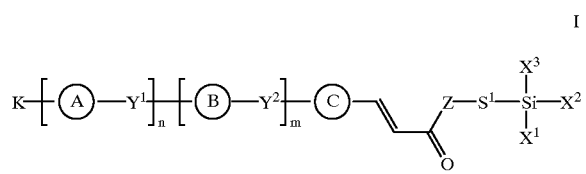

in which:

$X^1$, $X^2$ and $X^3$ denote alkyl, alkoxy or halogen, but at least one of these radicals in either alkoxy or halogen:

$S^1$ denotes a spacer unit or denotes a chain of the formula —$(CH_2)_r$—L—$(CH_2)_s$—, in which L denotes a single bond or linking functional groups, such as O, COO, OOC, $NR^1$, $NR^1$—CO—, CO—$NR^1$, $NR^1$—COO, OCO—$NR^1$, $NR^1$—CO—$NR^1$, —CH=CH— or —C≡C—, $R^1$ denotes hydrogen or lower alkyl and r and s each represent an integer from 1 to 20, with the proviso that r+s is ≦25;

Ring A denotes unsubstituted or fluorine-, chlorine-, cyano-, alkyl- or alkoxy-substituted phenylene, pyrid-2,5-diyl, pyrimidin-2,5-diyl, 1,3-dioxane-2,5-diyl, cyclohexane-1,4-diyl, piperidin-1,4-diyl or piperazin-1,4-diyl, it being possible for the alkyl and/or the alkoxy substituent to be mono- or polysubstituted by fluorine;

Ring B denotes unsubstituted or fluorine-, chlorine-, cyano-, alkyl- or alkoxy-substituted phenylene, pyrid-2,5-diyl, pyrimidin-2,5-diyl, 1,4- or 2,6-naphthylene, 1,3-dioxane-2,5-diyl or cyclohexane-1,4-diyl, it being possible for the alkyl and/or the alkoxy substituent to be mono- or polysubstituted by fluorine;

K is hydrogen, fluorine, chlorine, cyano, nitro or a straight-chain or branched alkyl, alkoxy, alkyl-COO, alkyl-CO—$NR^2$ or alkyl-OCO group having 1 to 20 carbon atoms which is optionally substituted by fluorine, chlorine, cyano or nitro and in which optionally one $CH_2$ group or a plurality of non-neighboring $CH_2$ groups may be replaced by O, CH=CH or C≡C and in which $R^2$ denotes hydrogen or lower alkyl;

$Y^1$ and $Y^2$, independently of one another, denote a single covalent bond, —$(CH_2)_t$—, —O—, —CO—, —COO—, —O—OC—, —$NR^3$—, —CO—$NR^3$—, —$R^3N$—CO—, —$(CH_2)_u$—O—, —O—$(CH_2)_u$—, —$(CH_2)_u$—$NR^3$— or $NR^3$—$(CH_2)_u$—, in which $R^3$ denotes hydrogen or lower alkyl;

t denotes an integer from 1 to 4;

u denotes an integer from 1 to 3;

m and n, independently of one another, denote 0 or 1;

Ring C denotes unsubstituted or fluorine-, chlorine-, cyano-, alkyl- or alkoxy-substituted phenylene, pyrimidin-2,5- or 3,5-diyl, pyrid-2,5- or -2,4-diyl or -2,6-diyl, 2,5-thiophenylene, 2,5-furanylene, 1,4- or 2,6-naphthylene, it being possible for the alkyl and/or the alkoxy substituent to be mono- or polysubstituted by fluorine;

Z denotes —O— or —$NR^4$— and $R^4$ denotes hydrogen or lower alkyl.

14. A hybrid layer element, comprising a crosslinkable mixture having at least two components at least one of which is a photocrosslinkable silane derivative of the formula I:

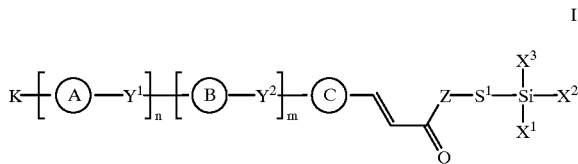

I in which:

$X^1$, $X^2$ and $X^3$ denote alkyl, alkoxy or halogen, but at least one of these radicals in either alkoxy or halogen:

$S^1$ denotes a spacer unit or denotes a chain of the formula —$(CH_2)_r$—L—$(CH_2)_s$—, in which L denotes a single bond or linking functional groups, such as O, COO, OOC, $NR^1$, $NR^1$—CO—, CO—$NR^1$, $NR^1$—COO, OCO—$NR^1$, $NR^1$—CO—$NR^1$, —CH=CH— or —C≡C—, $R^1$ denotes hydrogen or lower alkyl and r and s each represent an integer from 1 to 20, with the proviso that r+s is ≦25;

Ring A denotes unsubstituted or fluorine-, chlorine-, cyano-, alkyl- or alkoxy-substituted phenylene, pyrid-2,5-diyl, pyrimidin-2,5-diyl, 1,3-dioxane-2,5-diyl, cyclohexane-1,4-diyl, piperidin-1,4-diyl or piperazin-1,4-diyl, it being possible for the alkyl and/or the alkoxy substituent to be mono- or polysubstituted by fluorine;

Ring B denotes unsubstituted or fluorine-, chlorine-, cyano-, alkyl- or alkoxy-substituted phenylene, pyrid-2,5-diyl, pyrimidin-2,5-diyl, 1,4- or 2,6-naphthylene, 1,3-dioxane-2,5-diyl or cyclohexane-1,4-diyl, it being possible for the alkyl and/or the alkoxy substituent to be mono- or polysubstituted by fluorine;

K is hydrogen, fluorine, chlorine, cyano, nitro or a straight-chain or branched alkyl, alkoxy, alkyl-COO, alkyl-CO—NR or alkyl-OCO group having 1 to 20 carbon atoms which is optionally substituted by fluorine, chlorine, cyano or nitro and in which optionally one $CH_2$ group or a plurality of non-neighboring $CH_2$ groups may be replaced by O, CH=CH or C≡C and in which $R^2$ denotes hydrogen or lower alkyl;

$Y^1$ and $Y^2$, independently of one another, denote a single covalent bond, —$(CH_2)_t$—, —O—, —CO—, —COO—, —O—OC—, —$NR^3$—, —CO—$NR^3$—, —$R^3N$—CO—, —$(CH_2)_u$—O—, —O—$(CH_2)_u$—, —$(CH_2)_u$—$NR^3$— or $NR^3$—$(CH_2)_u$—, in which $R^3$ denotes hydrogen or lower alkyl;

t denotes an integer from 1 to 4;

u denotes an integer from 1 to 3;

m and n, independently of one another, denote 0 or 1;

Ring C denotes unsubstituted or fluorine-, chlorine-, cyano-, alkyl- or alkoxy-substituted phenylene, pyrimidin-2,5- or 3,5-diyl, pyrid-2,5- or -2,4-diyl or -2,6-diyl, 2,5-thiophenylene, 2,5-furanylene, 1,4- or 2,6-naphthylene, it being possible for the alkyl and/or the alkoxy substituent to be mono- or polysubstituted by fluorine;

Z denotes —O— or —$NR^4$— and $R^4$ denotes hydrogen or lower alkyl.

15. A silane as claimed in claim 1, wherein in $S^1$ the linking functional group L is O, COO, OOC, $NR^1$, $NR^1$—CO—, CO—$NR^1$, $NR^1$—COO, OCO—$NR^1$, $NR^1$—CO—$NR^1$, —CH=CH— or —C≡C—, where $R^1$ denotes hydrogen or lower alkyl.

16. A mixture as claimed in claim 5, wherein in $S^1$ the linking functional group L is O, COO, OOC, $NR^1$, $NR^1$—CO—, CO—$NR^1$, $NR^1$—COO, OCO—$NR^1$, $NR^1$—CO—$NR^1$, —CH=CH— or —C≡C—, where $R^1$ denotes hydrogen or lower alkyl.

17. A method as claimed in claim 9, wherein in $S^1$ the linking functional group L is O, COO, OOC, $NR^1$, $NR^1$—CO—, CO—$NR^1$, $NR^1$—COO, OCO—$NR^1$, $NR^1$—CO—$NR^1$, —CH=CH— or —C≡C—, where $R^1$ denotes hydrogen or lower alkyl.

18. A method as claimed in claim 10, wherein in $S^1$ the linking functional group L is O, COO, OOC, $NR^1$, $NR^1$—CO—, CO—$NR^1$, $NR^1$—COO, OCO—$NR^1$, $NR^1$—CO—$NR^1$, —CH=CH— or —C≡C—, where $R^1$ denotes hydrogen or lower alkyl.

19. An orientation layer as claimed in claim 11, wherein in $S^1$ the linking functional group L is O, COO, OOC, $NR^1$, $NR^1$—CO—, CO—$NR^1$, $NR^1$—COO, OCO—$NR^1$, $NR^1$—CO—$NR^1$, —CH=CH— or —C≡C—, where $R^1$ denotes hydrogen or lower alkyl.

20. A hybrid layer element as claimed in claim 12, wherein in $S^1$ the linking functional group L is O, COO, OOC, $NR^1$, $NR^1$—CO—, CO—$NR^1$, $NR^1$—COO, OCO—$NR^1$, $NR^1$—CO—$NR^1$, —CH=CH— or —C≡C—, where $R^1$ denotes hydrogen or lower alkyl.

21. An orientation layer as claimed in claim 13, wherein in $S^1$ the linking functional group L is O, COO, OOC, $NR^1$, $NR^1$—CO—, CO—$NR^1$, $NR^1$—COO, OCO—$NR^1$, $NR^1$—CO—$NR^1$, —CH=CH— or —C≡C—, where $R^1$ denotes hydrogen or lower alkyl.

22. A hybrid layer element as claimed in claim 14, wherein in $S^1$ the linking functional group L is O, COO, OOC, $NR^1$, $NR^1$—CO—, CO—$NR^1$, $NR^1$—COO, OCO—$NR^1$, $NR^1$—CO—$NR^1$, —CH=CH— or —C≡C—, where $R^1$ denotes hydrogen or lower alkyl.

\* \* \* \* \*

UNITED STATES PATENT AND TRADEMARK OFFICE
CERTIFICATE OF CORRECTION

PATENT NO. : 6,277,502 B1
DATED : August 21, 2001
INVENTOR(S) : Buchecker et al.

It is certified that error appears in the above-identified patent and that said Letters Patent is hereby corrected as shown below:

Column 18,
Line 62, "methyl]cinnamate" should read -- methoxy]cinnamate --.

Column 19,
Line 60, after "lower alkyl", insert a comma.

Column 20,
Line 67, "in either" should read -- is either --.

Column 21,
Lines 3-6, "groups, such as O, COO, OOC, NR1, NR1–CO–, CO– NR1, NR1–COO, OCO–NR1, NR1–CO–NR1,   –CH=CH–  or –C≡C–, R1 denotes hydrogen or lower alkyl" should read -- group --.
Line 18, "2,6-naphthylence" should read -- 2,6-naphthylene --.
Lines 32-33, "–R3– N–CO–" should read -- –R3N–CO– --.
Line 34, "NR3–(CH2)d–" should read -- NR3–(CH2)u– --.
Line 41, "phenylene;" should read -- phenylene, --.
Line 49, "producing of orientation layers" should read
-- producing an orientation layer --.
Line 65, "in either" should read -- is either --.

Column 22,
Lines 1-4, "groups, such as O, COO, OOC, NR1, NR1–CO–, CO–NR1, NR1–COO, OCO–NR1, NR1–CO–NR1, –CH=CH–, or –C≡C–, R1 denotes hydrogen or lower alkyl" should read -- group --
Line 61, "in either" should read -- is either --.
Lines 64-67, "groups, such as O, COO, OOC, NR1, NR1–CO–, CO–NR1, NR1–COO, OCO–NR1, NR1–CO–NR1, –CH=CH– or –C≡C–, R1 denotes hydrogen or lower alkyl" should read -- group --.

Column 23,
Line 23, after "R2 denotes", delete the comma.
Line 57, "in either" should read -- is either --.
Lines 60-63, "groups, such as O, COO, OOC, NR1, NR1–CO–, CO–NR1, NR1–COO, OCO–NR1, NR1–CO–NR1, –CH=CH– or –C≡C–, R1 denotes hydrogen or lower alkyl" should read -- group --.

UNITED STATES PATENT AND TRADEMARK OFFICE
CERTIFICATE OF CORRECTION

PATENT NO. : 6,1277,502 B1
DATED : August 21, 2001
INVENTOR(S) : Buchecker et al.

It is certified that error appears in the above-identified patent and that said Letters Patent is hereby corrected as shown below:

Column 24,
Line 58, "in either" should read -- is either --.
Lines 62-65, "groups, such as O, COO, OOC, NR1, NR1–CO–, CO–NR1, NR1–COO, OCO–NR1, NR1–CO–NR1, –CH=CH– or –C≡C–, R1 denotes hydrogen or lower alkyl" should read -- group --.

Column 25,
Line 59, "in either" should read -- is either --.
Lines 62-65, "groups, such as O, COO, OOC, NR1, NR1–CO–, CO–NR1, NR1–COO, OCO–NR1, NR1–CO–NR1, –CH=CH– or C≡C–, R1 denotes hydrogen or lower alkyl" should read -- group --.

Column 26
Line 18, "alkyl-CO–NR" should read -- alkyl-CO–NR2 --.

Signed and Sealed this

Twenty-third Day of July, 2002

Attest:

JAMES E. ROGAN
Attesting Officer         Director of the United States Patent and Trademark Office